(12) United States Patent
Birnbaum

(10) Patent No.: US 7,135,194 B2
(45) Date of Patent: Nov. 14, 2006

(54) SUBUNGUICIDE, AND METHOD FOR TREATING ONYCHOMYCOSIS

(76) Inventor: Jay E. Birnbaum, 26 Cheyenne Dr., Montville, NJ (US) 07045

( * ) Notice: Subject to any disclaimer, the term of this patent is extended or adjusted under 35 U.S.C. 154(b) by 377 days.

(21) Appl. No.: 10/671,307

(22) Filed: Sep. 25, 2003

(65) Prior Publication Data

US 2004/0062733 A1   Apr. 1, 2004

(51) Int. Cl.
*A61K 9/14*    (2006.01)
(52) U.S. Cl. .......................... 424/484; 424/61
(58) Field of Classification Search ............... None
See application file for complete search history.

(56) References Cited

U.S. PATENT DOCUMENTS

| | | | |
|---|---|---|---|
| 4,180,058 A * | 12/1979 | Brem ..................... | 128/898 |
| 4,250,164 A | 2/1981 | Bernstein | |
| 5,063,049 A | 11/1991 | Hillings | |
| 5,696,105 A | 12/1997 | Hackler | |
| 6,043,063 A | 3/2000 | Kurdikar | |
| 6,143,794 A | 11/2000 | Chaudhuri | |
| 6,162,420 A | 12/2000 | Bohn | |
| 6,231,840 B1 * | 5/2001 | Buck ..................... | 424/61 |
| 6,264,927 B1 | 7/2001 | Monahan | |
| 6,361,785 B1 | 3/2002 | Nair | |
| 6,846,837 B1 * | 1/2005 | Maibach et al. .......... | 514/350 |

| | | |
|---|---|---|
| 2002/0183387 A1 | 12/2002 | Bogart |
| 2003/0007939 A1 | 1/2003 | Murad |

FOREIGN PATENT DOCUMENTS

WO    WO 98/52927    11/1998

OTHER PUBLICATIONS

American Academy of Dermatology disclosure International Study Measures Quality of Life for Onychomycosis Patients Sep. 22, 1999.*
Stedman's Medical Dictionary 27th Edition "hyponychium" disclosure, downloaded from the world wide web at www.theonsonhc.com/pdrel/librarian/PFDfaultActionld/pdrcommon.stedmans on May 4, 2006.*

* cited by examiner

*Primary Examiner*—Michael P. Woodward
*Assistant Examiner*—Eric E. Silverman
(74) *Attorney, Agent, or Firm*—Bradley N. Ruben

(57) ABSTRACT

Onychomycosis is a fungal infection of the nail bed and is difficult to treat topically because penetration of the nail plate is difficult, and systemic antifungal treatments are prone to side effects and drug interactions.

The present invention treats onychomycosis by applying an antifungal composition to the nail bed directly using a solid, semi-solid, or flowable carrier. The carrier can be in the form of a semi-solid into which the user digs and scrapes the nail, a solid carrier can be inserted directly under the nail in contact with the nail bed, or a flowable composition can be injected in contact with the nail bed.

9 Claims, No Drawings

SUBUNGUICIDE, AND METHOD FOR TREATING ONYCHOMYCOSIS

BACKGROUND OF THE INVENTION

1. Field of the Invention

This invention relates to articles of manufacture and to methods for the subungual (under the nail) treatment of infections, especially fungal infections, of the toenails and fingernails (onychomycosis).

2. The State of the Art

Fungi are eukaryotic cells that may reproduce sexually or asexually and may be biphasic, with one form in nature and a different form in the infected host. Fungal diseases are referred to as mycoses.

A fungal infection of the nails, commonly referred to as onychomycosis, is most frequently caused by dermatophytes (most commonly *Trichophyton rubrum*) but also can be caused by molds and *Candida*. Mixed infections also occur. There are several forms of onychomycosis: distal lateral subungual (DLSUO), white superficial, proximal subungual, endonyx, and candidal. The most common form is DLSUO in which the fungus spreads from the plantar skin and invades the underside of the nail via the hyponychium and distal lateral nail bed. Inflammation involving these areas produces the characteristic signs of the disease including a thickened and discolored nail plate, nail bed hyperkeratosis, and onycholysis (a separation or loosening of the nail plate from the nail bed which starts at the distal free margin and progresses proximally as the infection moves proximally). Onychomycosis may cause pain and discomfort especially (in the case of toenail DLSUO) with standing, walking, and exercise, some loss of dexterity (in the case of fingernail DLSUO), and is often associated with embarrassment and diminished self-esteem. The onychomycotic nail also serves as a reservoir for dermatophytes and contributes to treatment failure and recurrence of *tinea pedis*.

The majority of known antifungal agents fall into one of three main groups. One major group includes polyene derivatives, including amphotericin B and the structurally related compounds nystatin and pimaricin, which are only administered intravenously. The unrelated antifungal agent flucytosine (5-fluorocytosine, a diazine), an orally absorbed drug, is frequently used as an adjunct to amphotericin B treatment for some forms of candidiasis and cryptococcal meningitis.

A second major group of antifungal agents is the azole derivatives. This group of agents includes ketoconazole (U.S. Pat. Nos. 4,144,346 and 4,223,036), fluconazole (U.S. Pat. No. 4,404,216), itraconazole (U.S. Pat. No. 4,267,179), voriconazole, bifonazole, clotrimazole, miconazole, econazole, butoconazole, oxiconazole, sulconazole, terconazole, liarozole, and irtemazol. U.S. Pat. No. 6,277,873 describes substituted thiazole, thiadiazole, and oxadiazole antifungals.

A third major group of antifungal agents includes the fungicidal allylamines such as naftifine (Naftin), terbinafine (EP 24,587-A1; Lamisil), and the benzylamine butenafine (Mentax).

Various other types of antifungal agents are known. Griseofulvin is a fungistatic agent which is administered orally for fungal infections of skin, hair or nails that do not respond to topical treatment. Still other antifungal agents include thiocarbonate tolnaftate, ciclopirox, sulbentine, and morpholines, e.g., amorolfine, and the related morpholines disclosed in U.S. Pat. No. 5,120,530, and the 1-hydroxy-2-pyridone compounds disclosed in U.S. Pat. No. 4,957,730. Like the allylamines and azoles, tolnaftate blocks synthesis of ergosterol.

It has also been known to combine antifungal agents with anti-inflammatory agents. The steroidal anti-inflammatory agent may be selected from among any of the known steroidal anti-inflammatory agents, including, for example, any of those disclosed in *The Merck Index* or in U.S. Pat. Nos. 5,002,938, 5,110,809, and 5,219,877. Examples of steroidal anti-inflammatory agents useful in combination with antifungals can include 21-acetoxypregnenolone, alclometasone or its dipropionate salt, algestone, amcinonide, beclomethasone or its dipropionate salt, betamethasone and salts thereof, including, for example, betamethasone benzoate, betamethasone dipropionate, betamethasone sodium phosphate, betamethasone sodium phosphate and acetate, and betamethasone valerate; clobetasol or its propionate salt, clocortolone pivalate, hydrocortisone and salts thereof, including, for example, hydrocortisone acetate, hydrocortisone butyrate, hydrocortisone cypionate, hydrocortisone phosphate, hydrocortisone sodium phosphate, hydrocortisone sodium succinate, hydrocortisone tebutate and hydrocortisone valerate; cortisone acetate, desonide, desoximetasone, dexamethasone and salts thereof, for example, acetate and sodium phosphate; diflorasone diacetate, fludrocortisone acetate, flunisolide, fluocinolone acetonide, fluocinonide, fluorometholone, flurandrenolide, halcinonide, medrysone, methylprednisolone and salts thereof, e.g., acetate, sodium succinate; mometasone furoate, paramethasone acetate, prednisolone and salts thereof, e.g., acetate, diethylaminoacetate, sodium phosphate, sodium succinate, tebutate, trimethylacetate; prednisone, triamcinolone and derivatives thereof, e.g., acetonide, benetonide, diacetate, hexacetonide. Other glucocorticoid steroids reported in the literature, including The Merck Index, or otherwise approved by the local drug regulatory agency, e.g., Food and Drug Administration, may also be used. Preferred steroidal anti-inflammatory agents usually include clobetasol and its salts, e.g., propionate salt; betamethasone and its salts, hydrocortisone and its salts, and triamcinolone and its salts, although as new steroidal anti-inflammatories are developed and reviewed, preferences may change. The anti-inflammatory agent will usually be present in a topical composition in combination with an antifungal in an amount within the range of 0.01 to about 5 percent, preferably from about 0.1 to 2 percent, based on the total weight of the composition.

Thus, various types of antifungal agents and their combination with steroidal anti-inflammatory agents are known.

In spite of the wide varieties of anti-fungal that are available and their use in combination with other active ingredients, onychomycosis is difficult to treat. Since on most ocassions onychomycosis (i.e., the distal lateral subungual form) is a disease of the nail bed underlying the nail plate, the condition is best treated systemically ("from the inside") because topical access to the nail bed is restricted by the relatively impermeable nail plate. Consequently, onychomycosis can be treated effectively in many patients using systemic (oral) medications such as terbinafine (Lamisil) and itraconazole (Sporonox). Fluconazole (Diflucan), although not FDA approved, is also used in some patients. These newer drugs have supplanted oral forms of ketoconazole and griseofulvin, which were previously used to treat the disease. However the systemic (oral) medicines must be administered for several months for elimination of the infection and regrowth of new nail. These drugs may also produce serious side effects, and they may interact with other medications. Accordingly, systemic medications for treating onychomycosis are unacceptable for many patients. For those patients, the only available route of administration is topical.

Nail lacquers for the treatment of onychomycoses and similar fungal infections affecting nails (toe nails and/or finger nails) of humans, in particular, or other animals, are known. Representative examples are described in the patent literature, such as the following U.S. Pat. No. 4,957,730 (1-hydroxy-2-pyridone in water-insoluble film-former); U.S. Pat. No. 5,120,530 (amorolfine in quaternary ammonium acrylic copolymer); U.S. Pat. No. 5,264,206 (tioconazole, econazole, oxiconazole, miconazole, tolnaftate, naftifine hydrochloride, in water-insoluble film-former); U.S. Pat. No. 5,346,692 (with urea and dibutyl phthalate plasticizer); U.S. Pat. No. 5,487,776 (griseofulvin as colloidal suspension). U.S. Pat. No. 6,224,887, teaches a nail lacquer for onychomycosis with the combination of antifungal and a certain penetration-enhancing medium carbon chain dioxane or acetal. PENLAC brand ciclopirox is the only FDA-approved topical treatment approved in the United States for onychomycosis. Topical products approved for use outside of the United States include a lacquer of amorolfine and a combination of bifonazole Other U.S. Pat. Nos. which relate to antifungal products include, for example: U.S. Pat. No. 4,636,520 (combination of imidazole and pyrrolnitrin); U.S. Pat. No. 5,002,938 (gel, combination of imidazole and 17-ester corticosteroid anti-inflammatory agent); 5,110,809 (antifungal gel plus steroid); U.S. Pat No. 5,219,877 (gel product with imidazole antifungal optionally with steroidal anti-inflammatory, in a vehicle system that includes lauryl alcohol); U.S. Pat. No. 5,391,367 (aqueous alcoholic gel with tioconazole); U.S. Pat. No. 5,464,610 (salicylic acid plaster); and U.S. Pat. No. 5,696,105 (mometasone furoate).

U.S. Pat. No. 6,207,142 describes antifungal shampoos.

U.S. Pat. No. 5,894,020, discloses an antifungal bar soap for treating *tinea pedis*.

Anatomically, the "nail" that is seen is technically the nail plate. At the most proximal end is the matrix (root), from which the nail grows, and the eponychium (the cuticle) which forms a seal between the skin and the nail plate. At the distal end, between the nail plate and the skin, is the hyponychium. The nail plate presents a considerable barrier to penetration and hence limits access to the nail bed for products applied topically to the nail plate. Current topical therapies have such low penetration through the nail plate that they have a very low efficacy (less than 10% even after prolonged application). These therapies do not appear to exhibit characteristic concentration-response or time-response relationships. This suggests that in the small percentage of people in whom these topical treatments are effective, efficacy may not be related to penetration through the nail. Materials such as urea increase the penetration of the medication through the nail plate, but such materials alter the nail and disrupt its integrity.

SUMMARY AND OBJECTS OF THE INVENTION

In light of the forgoing, it would benefit the treatment of onychomycosis to administer an antifungal agent in closer proximity to the nail bed, and to decrease the barriers to access to the nail bed to treat the condition. As mentioned above, there is a small population that is helped by topical treatment, in spite of low penetration through the nail. Successful treatment in those people suggests that administration in contact with the nail bed and/or cutting/manipulation of the nail may have significantly contributed to a favorable outcome. Accordingly, a more reasonable approach to topical treatment, especially in cases where only the distal two thirds (or less) of the nail bed is involved, is with subungual treatment.

Accordingly, in one embodiment this invention provides a method for treating onychomycosis by administering an antifungal subungually.

In order to practice this treatment without the need for invasive procedures or compromising the nail, another embodiment of this invention provides a solid or semisolid material that is placed in contact with the nail bed

DESCRIPTION OF SPECIFIC EMBODIMENTS

Antifungal agents and various compositions containing the same are described in the Background section, and the patents and literature references mentioned therein are incorporated herein by reference.

By this invention, a solid or semisolid material having a fungicidal or fungistatic agent is placed in contact with the nail bed and preferably forced under the nail. Placing the antifungal in such close proximity provides the preferred direct contact between the infected area and the therapeutic agent. In addition, having a small reservoir of antifungal agent facilitates diffusion of antifungal proximally and laterally along the nail bed. Localized therapy in this fashion circumvents the nail plate, a limiting factor in the efficacy of topical products which are applied to the outer surface of the nail plate, and of course avoids problems with the present systemic therapies (potentially serious side effects and interactions with concomitant medications). As noted in the Background section, the manufacture of bar soaps, shampoos, and gels having antifungal agents is known. It is also well-known how to formulate caulks, pastes, and creams (such as topical delivery creams and dentifrices) and semi-solids (such as deodorant and antiperspirant/deodorant sticks) for cosmetic and pharmaceutical applications.

As one example, a bar soap is made having a desired antifungal agent, or combination of antifungal agents, and optionally other active (e.g., anti-inflammatory) agents and/or inactive agents (e.g., colorants, fragrances, conditioners, humectants). The bar is used by having the patient scratch the bar with the infected nail(s) effective to cause the soap under the nail and in contact with the nail bed. The antifungal agent can be suspended in the soap, and/or it can be dispersed as solid particles. The physical properties of the soap, such as hardness (within the range of hardnesses that soaps can be manufactured; hardness being measured on a scale such as the Mho hardness scale) can be adjusted to facilitate the penetration of the soap under the nail. The soap "carrier" for the antifungal can be made of a material that softens or even melts slowly at the surface temperature under the nail.

Similarly, semisolid carriers (such as are employed in "stick" deodorants and antiperspirants) can be formulated as desired to deliver the antifungal by having the patient scratch the substance or by pressing/rubbing the substance under the distal nail.

Likewise, a caulk or paste, or a gel, can be forced under the nail. The rheology of such a material can be adjusted to facilitate its being forced subungually between the nail plate and the nail bed when dispensed as it experiences different shear rates when under the nail confines than when flowing through the dispenser outlet.

In a similar embodiment, a more flowable composition, such as a cream, ointment, solution, or suspension can be placed under the nail by means of an applicator inserted between the nail bed and the nail plate. Such an applicator can be a hypodermic needle or similar device for injecting by pressure, a cannula through which a sponge or other porous carrier is inserted, or other small tube through which the antifungal may be carried.

In an analogous manner, a small strip or pellet can be placed under the nail in contact with the nail bed, or force between the nail plate and the nail bed. The strip or pellet can be a polymer coated with an antifungal, or a hard sponge or porous polymer coated and/or infiltrated with an antifungal, or any other excipient sufficiently hard to be placed under the nail, and preferably to be forced at least partially between the nail plate and the nail bed.

For those administration devices that can be forced between the nail plate and the nail bed, the addition of a topical anesthetic and/or short-acting vasoconstrictor (to minimize bleeding) may be desirable.

Thus, while the prior art attemts to treat the condition systemically or locally, through the nail plate, or transhyponychium, the present invention accesses the nail bed by administration just proximal of the hyponychium by going between the hyponychium and the nail plate. During onychomycosis, onycholysis, or lifting of the nail plate from the nail bed, is a frequent occurrence. The subungual mode of application capitalizes on the phenomenon of onycholysis inasmuch as the resulting space between the nail plate and the hyponychium allows the medication to be forced past (over) the hyponychium and administered to the distal part of the nail bed, from where it will diffuse or migrate proximally and laterally.

Yet another method for delivering the medication is with a jet injector (high pressure injection). Such devices are typically used for insulin (in diabetes patients) and for innoculations, and force the liquid substance to be delivered through the skin. For the present invention, a jet injector, preferably adapted to provide a nozzle suitable for contact with the hyponychium, can be used to administer the medication directly to the nail bed.

After administration of the medication, the subungual area can be occluded, such as with a small bandage (physical and/or a film-forming substance). A finger cot or a glove (for a hand or foot (i.e., a sock with separate extensions for each toe)) can be used to occlude the end of the finger or toe, or multiple fingers or toes.

The amount of the active antifungal agent or mixture of such agents in the composition will depend on such factors as its structure and antimicrobial activity, release rate from the soap/gel/paste/solid carrier, and diffusion characteristics, which characteristics are generally well-known or can be readily determined or estimated. Generally, any amount of the agent effective to kill or inhibit the infecting microorganism, which will generally be several to several tens to hundreds (or more) times greater than the Mean Inhibitory Concentration (MIC), may be included in the composition as applied. Typically, amounts of active antifungal agent in the range of from about 0.5 to 20 percent by weight, preferably from about 1 to 10 percent, by weight, of the total composition.

The present composition and method can also use a keratolytic agent to facilitate diffusion or migration of the medication through the subungual debris, caused during the above-described hyperkeratosis. Suitable keratolytic agents include urea (5–40%), salicylic acid (5–40%), DMSO, sulfur, and other known compounds. Acid and/or enzymatic keratolytics can be used. The acids include the alpha-hydroxy acids, alpha-keto acids, beta-hydroxy acids and their derivatives including the root moieties glycolic, lactic, pyruvic, and citric. In addition, such derivatives can include salts, such as ammonium lactate (commercially available as LacHydrin). Examples of enzymatic exfoliants useful in the compositions and methods of the invention include, but are not limited to, papain, from papaya, and bromalein, from pineapple. Examples of acidic exfoliants include, but are not limited to, a mono- or poly-hydroxy acid, tannic acid, or a mixture thereof, or a pharmaceutically acceptable salt or ester thereof. One of ordinary skill in the art will be readily able to select and prepare suitable mono- or poly-hydroxy acids for use in the composition of the invention, for example, alkyl hydroxycarboxylic acids, aralkyl and aryl hydroxycarboxylic acids, polyhydroxy-carboxylic acids, and hydroxy-polycarboxylic acids. One of ordinary skill in the art would typically select one or more of the following mono- or poly-hydroxy acids: 2-hydroxyacetic acid (glycolic acid); 2-hydroxypropanoic acid (lactic acid); 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxyacetic acid; 2,3-dihydroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxymandelic acid; 4-hydroxy-3-methoxymandelic acid; 2-hydroxy-2-methylbutanoic acid; 3-(2-hydroxyphenyl) lactic acid; 3-(4-hydroxyphenyl) lactic acid; hexahydromandelic acid; 3-hydroxy-3-methylpentanoic acid; 4-hydroxydecanoic acid; 5-hydroxydecanoic acid; aleuritic acid; 2-hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutaned-ioic acid; citric acid, isocitric acid, agaricic acid, quinic acid, glucoronic acid, glucoronolactone, galactoronic acid, galactoronolactone, uronic acids, uronolactones, ascorbic acid, dihydroascorbic acid, dihydroxytartaric acid, tropic acid, ribonolactone, gluconolactone, galactonolactone, gulonolactone, mannonolactone, citramalic acid; pyruvic acid, hydroxypyruvic acid, hydroxypyruvic acid phosphate and esters thereof; methyl pyruvate, ethyl pyruvate, propyl pyruvate, isopropyl pyruvate; phenyl pyruvic acid and esters thereof; methyl phenyl pyruvate, ethyl phenyl pyruvate, propyl phenyl pyruvate; formyl formic acid and esters thereof; methyl formyl formate, ethyl formyl formate, propyl formyl formate; benzoyl formic acid and esters thereof; methyl benzoyl formate, ethyl benzoyl formate and propyl benzoyl formate; 4-hydroxybenzoyl formic acid and esters thereof; 4-hydroxyphenyl pyruvic acid and esters thereof, and 2-hydroxyphenyl pyruvic acid and esters thereof.

As mentioned above, acceptable salts of the foregoing acids can be used as keratolytic agents. Examples of suitable inorganic metallic bases for salts formation with the acid compounds of the invention include, but are not limited to, ammonium, aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), and procaine.

It should be understood that one or more derivatives of the above acidic component, such as esters or lactones thereof, are also suitably used. One of ordinary skill in the art will also understand that various hydroxy acids described in U.S. Pat. Nos. 5,547,988 and 5,422,370, the disclosures of which are incorporated herein by reference, are also suitable for use in the compositions and methods of the invention. The acidic component is present in the composition and methods in an amount sufficient to exfoliate, i.e., loosen and especially remove dead or dying cells from at least a portion of the nail bed. The acidic component is typically present in an amount from about 0.1 to 12 weight percent, preferably about 1 to 11 weight percent, more preferably from about 4 to 10 weight percent of the composition. For example, the acidic component may be from about 0.1 to 3 weight percent citric acid in combination with up to about 2 weight percent salicylic acid.

The instant composition is preferably applied between twice daily and once weekly, more preferably between once daily and once every three days. It is also preferred that the doses be self-administered.

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A method for treating onychomycosis, comprising providing a subunguicide including an antifungal agent in a suitable carrier, and administering the same subungually by forcing the subunguicide between the hyponychium and the nail plate and past the hyponychium to be in contact with the nail bed.

2. The method of claim 1, wherein the subunguicide is placed between the nail plate and the nail bed.

3. The method of claim 1, wherein the carrier is a solid or a semi-solid.

4. The method of claim 1, wherein the antifungal agent and carrier subunguicide is provided as a flowable composition selected from gels, creams, lotions, solutions, and suspensions.

5. The method of claim 4, further comprising:

providing an applicator having a reservoir for holding an amount of the antifungal agent in the suitable carrier and a tube through which the agent and carrier can flow from the reservoir to the end of the tube; placing the tube in contact with the nail bed without penetrating the nail plate; and causing the antifungal agent and carrier to flow through the tube and reside in contact with the nail bed.

6. The method of claim 1, further comprising the co-administration of a systemic antifungal agent.

7. The method of claim 1, wherein the carrier is flowable and is administered subungually by high pressure injection.

8. The method of claim 1, wherein the carrier is flowable and is forced between the nail plate and the hyponychium past the hyponychium to reside in contact with the nail bed.

9. The method of claim 1, wherein the carrier is solid or semi-solid and is forced between the nail plate and the hyponychium past the hyponychium to reside in contact with the nail bed.

\* \* \* \* \*